United States Patent [19]

Caldwell

[11] Patent Number: Plant 6,145

[45] Date of Patent: Apr. 5, 1988

[54] SPATHIPHYLLUM NAMED 'LYNISE'

[75] Inventor: E. Bond Caldwell, Brooksville, Fla.

[73] Assignee: Hartman's Plants, Inc., Sebring, Fla.

[21] Appl. No.: 815,687

[22] Filed: Jan. 2, 1986

[51] Int. Cl.[4] ..... A01H 5/00

[52] U.S. Cl. ..... Plt./88

[58] Field of Search ..... Plt./88

*Primary Examiner*—James R. Feyrer

*Attorney, Agent, or Firm*—Irving N. Feit

[57] ABSTRACT

Disclosed is a new and distinct variety of Spathiphyllum which is particularly distinguished by having rapid growth and a propensity to sucker as compared to related plants. The plant is a selection from the cross Mauna Loa 'Alice'×floribundum (seed parent) and wallisi (pollen parent).

1 Drawing Sheet

The invention comprises a new and distinct cultivar of Spathiphyllum known as Spathiphyllum hybrida 'Lynise'.

The new cultivar is a product of a planned program carried out by Bond Caldwell of Babylon Nursery, Brooksville, Fla. The parents are (Mauna Loa 'Alice'×floribundum) (seed parent) and wallisii (pollen parent). The cultivar was discovered and selected from the progeny of the stated cross by Mr. Caldwell. Asexual propagation by division (Mr. Caldwell) and by tissue culture (Hartman's Plants, Inc.) was used to increase the number of plants available for evaluation and to demonstrate the stability of the distinguishing combination of characteristics from generation to generation.

The following observations, measurements and values describe plants grown in Brooksville under greenhouse conditions that closely approximate those generally used in horticultural practice.

The following traits have been repeatedly observed and are characteristics that in combination distinguish Spathiphyllum hybrida 'Lynise' from other Spathiphyllum of the general type i.e. Mauna Loa 'Supreme' and 'St. Mary's'. Mauna Loa 'Supreme' and 'St. Mary's' are trademarks of Olgesby Lab, Inc.

DISTINCTIONS

1. Medium large Spathiphyllum of smaller size than 'St. Marys's' and approximately the same size but somewhat taller than 'Supreme' being approximately 0.7 meters to 1.0 meters in height and approximately 1.0 meters to 1.4 meters in width when fully mature in a 15 gallon pot.

2. White flowers, the spathe being approximately 20 cm to 28 cm in height and approximately 9.0 cm to 12.00 cm in width standing above the soil surface 0.9 meters to 1.1 meters to the base of the spathe in a 15 gallon container.

3. Closely spaced prominant veins giving a more corragated appearance than 'Supreme' or 'St. Mary's'. The veination pattern described above is apparent in all of the leaves of mature size on 'Lynise' without significant exception, although there may be a few gaps in the pattern in some of the leaves. Some cultivars such as 'supreme' may have a few leaves that partially approximate the pattern. When the plants are viewed as a whole, however, they are clearly distinguishable.

4. The petiole, midrib and primary veins are stiff enough to resist wilting due to moderate water stress as compared to 'Supreme'.

5. The lower leaves are rounder than 'Supreme' giving the mature plant a fuller appearance.

6. Lynise' suckers more than 'Supreme'.

7. Lynise' does not pale as much as 'Supreme' during the winter.

8. Lynise' has thicker leaf blades than 'Supreme'.

BRIEF DESCRIPTION OF THE DRAWING

The single FIGURE of drawing depicts a single specimen of 'Lynise' in approximate sideview, with six spathes present in various attitudes and stages.

DESCRIPTION (All color references are measured against The Royal Horticultural Society Colour Chart).

Origin: Seedling.

Botanic classification: Spathiphyllum hybrida 'lynise'.

Propagation: Asexual reproduction either through tissue culture or division.

Plant: In a 15 gallon pot, 'Lynise' will be at the mature size of approximately 0.7 meters to 1.0 meters in height and approximately 1.0 to 1.4 meters in width after approximately 50 weeks to 62 weeks under the appropriate growing conditions from tissue culture.

Leaves:

*Form.*—The leaf blade is simple elliptic with an apice having aristate tendencies and a cuneate base.

*Size and width.*—Leaf blades of a mature sized plant will be approximately 35 cm to 45 cm in length and approximately 12 cm to 20 cm in width.

*Petiole.*—The petiole will be approximately 32 cm to 45 cm in height from the soil surface to the base of the leaf blade. The petiole will be 6 mm to 10 mm in diameter.

*Texture.*—Leaves will be less glossy than 'St. Mary's' or 'Supreme'. Leaves will be somewhat stiffer and thicker than 'St. Mary's' or 'Supreme'.

*Veins.*—Well defined, closely spaced sunken veins giving a corragated appearance. Well defined veins on mature sized leaves are approximately 6 mm to 10 mm apart and stand prominately out on the abaxial side. This pattern may not be evident in leaves less than the mature size. This veination pattern is distinct from the veination pattern of 'St. Mary's', but may be approximated by a few leaf sections of 'Supreme'.

Color: Mature leaf: Adaxial side 147A, 137A. Abaxial side 137B, 137C.

Immature leaf: Adaxial side 138C, 138B. Abaxial side 147B.

Inflorescence:

*Immature.*—The spathe is tightly rolled around the spadix and extrudes from the petiole sheath. The spathe is fully open approximately when the pedicel is fully elongated approximately 0.9 meters to 1.1 meters from soil surface to base of spathe.

Mature spathe:

*Size.*—The spathe is approximately 20 cm to 28 cm in height and approximately 9.0 cm to 12.0 cm in width.

*Color.*—The color is 155D turning to 138B as the spathe matures.

*Arrangement.*—The spathe stands up on straight wiry pedicels and opens vertically above the leaves.

*Shape.*—The spathe is roundish to oval with an aristate apice. It is slightly cupped.

*Flowering time.*—After approximately 9 months to 11 months from tissue culture for an untreated plant and depending on season, 1 to 3 blossoms are present. Smaller blossoms may occur on less mature growth.

Reproductive organs:

*Spadix.*—Size: Approximately 7 cm to 10 cm in height and approximately 18 mm to 25 mm in diameter. Color: 158C changing to 147A as the spadix matures.

*Stamens.*—Anthers and filaments not clearly visible.

*Pollen.*—158C in color.

*Pistle.*—158C in color, protruding between the staminate flowers, firmly fixed to the main axle. The pistilate flowers extend approximately 2 mm to 4 mm beyond the staminate flowers.

Roots: White fleshy main roots with finer laterals.

GENERAL OBSERVATIONS

Spathiphyllum 'Lynise' is a faster growing Spathiphyllum than cultivars 'St. Mary's' or 'Supreme' that suckers as a mature single plant and forms a dense mass when propagated from tissue culture clumps. It is medium green, about the same color as 'Supreme' but darker than 'St. Mary's'. It is about the same size but taller than 'Supreme' and smaller than 'St. Mary's'. 'Lynise', in combination with the characteristics described above, is a unique new cultivar.

I claim:

1. A new and distinct cultivar of Spathiphyllum as described and illustrated.

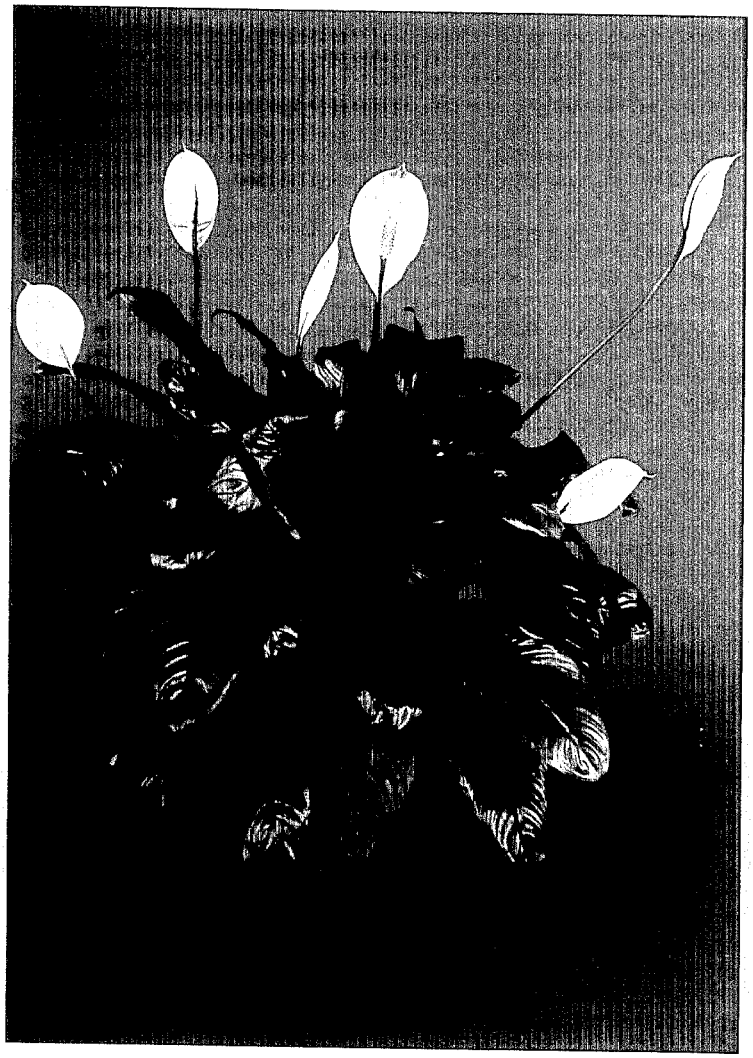

* * * * *